US011364364B2

(12) United States Patent
Rickheim et al.

(10) Patent No.: US 11,364,364 B2
(45) Date of Patent: Jun. 21, 2022

(54) BIOSTIMULATOR TRANSPORT SYSTEM HAVING VALVE BYPASS TOOL

(71) Applicant: PACESETTER, INC., Sylmar, CA (US)

(72) Inventors: David Rickheim, Bloomington, MN (US); Scott M. Smith, Monticello, MN (US)

(73) Assignee: PACESETTER, INC., Sylmar, CA (US)

( * ) Notice: Subject to any disclaimer, the term of this patent is extended or adjusted under 35 U.S.C. 154(b) by 253 days.

(21) Appl. No.: 16/528,264

(22) Filed: Jul. 31, 2019

(65) Prior Publication Data

US 2020/0345982 A1 Nov. 5, 2020

Related U.S. Application Data

(60) Provisional application No. 62/843,134, filed on May 3, 2019.

(51) Int. Cl.
*A61M 25/00* (2006.01)
*A61M 25/01* (2006.01)
(Continued)

(52) U.S. Cl.
CPC .... *A61M 25/0068* (2013.01); *A61M 25/0136* (2013.01); *A61M 25/0662* (2013.01);
(Continued)

(58) Field of Classification Search
CPC .......... A61M 25/0068; A61M 25/0136; A61M 25/0662; A61M 2025/0687;
(Continued)

(56) References Cited

U.S. PATENT DOCUMENTS 489,107 A 1/1893 Storz
5,782,807 A 7/1998 Falvai et al.
(Continued)

FOREIGN PATENT DOCUMENTS

WO 2012083245 A1 6/2012

OTHER PUBLICATIONS

U.S. Appl. No. 14/508,556, filed Oct. 7, 2014; Title: Delivery Catheter Systems and Methods.
(Continued)

*Primary Examiner* — Richard G Louis
(74) *Attorney, Agent, or Firm* — Womble Bond Dickinson (US) LLP

(57) ABSTRACT

A valve bypass tool, and a biostimulator transport system having such a valve bypass tool, is described. The valve bypass tool includes an annular seal to seal against a protective sheath of the biostimulator transport system. The valve bypass tool is slidably mounted on the protective sheath and includes a bypass sheath to insert into an access introducer. The valve bypass tool can lock onto the access introducer by mating a locking tab of the valve bypass tool with a locking groove of the access introducer. The locking tab can have a decent that securely fastens the components to resist decoupling when the biostimulator transport system is advanced through the access introducer into a patient anatomy. Other embodiments are also described and claimed.

19 Claims, 12 Drawing Sheets

(51) Int. Cl.
*A61M 25/06* (2006.01)
*A61N 1/375* (2006.01)
*A61N 1/05* (2006.01)

(52) U.S. Cl.
CPC ... *A61N 1/3756* (2013.01); *A61M 2025/0681* (2013.01); *A61M 2025/0687* (2013.01); *A61N 2001/058* (2013.01); *A61N 2001/0578* (2013.01)

(58) Field of Classification Search
CPC ......... A61M 2025/0681; A61N 1/0573; A61N 1/3756; A61N 2001/058; A61N 1/37518
See application file for complete search history.

(56) References Cited

U.S. PATENT DOCUMENTS

| | | | |
|---|---|---|---|
| 5,885,217 A | 3/1999 | Gisselberg et al. | |
| 6,408,214 B1* | 6/2002 | Williams | A61M 25/0041 607/122 |
| 6,695,816 B2 | 2/2004 | Cassidy, Jr. | |
| 6,808,509 B1* | 10/2004 | Davey | A61M 39/0606 604/164.05 |
| 7,985,232 B2* | 7/2011 | Potter | A61M 25/0668 606/129 |
| 8,043,263 B2 | 10/2011 | Helgeson et al. | |
| 9,149,606 B2 | 10/2015 | Beissel et al. | |
| 10,004,533 B2 | 6/2018 | Entabi | |
| 2004/0254534 A1* | 12/2004 | Bjorkman | A61M 39/0606 604/160 |
| 2005/0125030 A1* | 6/2005 | Forsberg | A61B 17/0057 606/213 |
| 2005/0171470 A1* | 8/2005 | Kucklick | A61B 1/317 604/96.01 |
| 2008/0300538 A1 | 12/2008 | Schweikert et al. | |
| 2018/0280703 A1 | 10/2018 | Hillukka et al. | |
| 2019/0224450 A1* | 7/2019 | Amar | A61M 25/09041 |
| 2020/0406025 A1* | 12/2020 | Guo | A61M 25/0668 |

OTHER PUBLICATIONS

U.S. Appl. No. 60/619,431, filed Jan. 19, 2018: Title: Locking Guide Catheter Hubs.

* cited by examiner

A-A

B - B

C - C

INSERT A BYPASS SHEATH OF A VALVE BYPASS TOOL, WHICH IS SLIDABLY MOUNTED ON A PROTECTIVE SHEATH OF A BIOSTIMULATOR TRANSPORT SYSTEM, INTO A PROXIMAL OPENING OF AN INTRODUCER CAP OF AN ACCESS INTRODUCER — 1702

TWIST THE VALVE BYPASS TOOL RELATIVE TO THE ACCESS INTRODUCER SUCH THAT A LOCKING TAB EXTENDING RADIALLY OUTWARD FROM A TOOL BODY OF THE VALVE BYPASS TOOL ENGAGES A LOCKING GROOVE IN THE INTRODUCER CAP — 1704

FIG. 17

BIOSTIMULATOR TRANSPORT SYSTEM HAVING VALVE BYPASS TOOL

This application claims the benefit of priority of U.S. Provisional Patent Application No. 62/843,134, filed May 3, 2019, entitled "Biostimulator Transport System Having Valve Bypass Tool," and that patent application is incorporated herein by reference in its entirety to provide continuity of disclosure.

BACKGROUND

Field

The present disclosure relates to biostimulators and related delivery and retrieval systems and methods. More specifically, the present disclosure relates to transport systems for delivery or retrieval of leadless biostimulators.

Background Information

Vascular access introducers are commonly used to gain access to a vasculature of a patient for a medical procedure. For example, a vascular access introducer having an introducer sheath and a dilator can be advanced through an incision in a vessel in order to enlarge the incision. The dilator can be removed while leaving the introducer sheath within the vessel to permit an interventional device, such as cardiac catheters or other catheter devices, to be passed through the sheath into the vessel. The introducer sheath can include a hemostasis valve to prevent blood from leaking out of the introducer sheath before or after the interventional device is advanced into the vessel.

Interventional devices may be damaged if passed directly through the hemostasis valve of the access introducer. For example, the interventional device may be a transport system used to deliver a leadless cardiac pacemaker to a pacing site. Leadless cardiac pacemakers incorporate electronic circuitry at the pacing site and eliminate leads, and thus, avoid many of the shortcomings of conventional cardiac pacing systems. When the leadless cardiac pacemaker passes through the hemostasis valve, it may be squeezed and damaged by the hemostasis valve. Accordingly, a bypass tube may be used to open the hemostasis valve such that the interventional device can be passed through the bypass tube into the patient anatomy. The bypass tube can hold the hemostasis valve open during device passage, and is removed from the hemostasis valve to allow the valve to close around the transport system to achieve hemostasis.

SUMMARY

Existing bypass tubes used to provide easier and safer introduction of leadless cardiac pacemakers into an access introducer can back out of the access introducer under certain conditions. For example, the hemostasis valve can exert a proximal force on the bypass tube, which can push the bypass tube back and away from the access introducer. Back out of the bypass tube can cause the hemostasis valve to collapse onto and damage the leadless cardiac pacemaker during passage.

A valve bypass tool and a biostimulator transport system having the valve bypass tool, is provided. The biostimulator transport system can be a catheter-based system for delivering or retrieving a leadless pacemaker. For example, the biostimulator transport system can be a biostimulator delivery system or a biostimulator retrieval system. The biostimulator transport system can include a handle and a deflectable catheter extending from the handle to a distal catheter end. A leadless pacemaker can connect to the distal end. A protective sheath can be slidably mounted on the deflectable catheter and include an atraumatic end to capture the leafless pacemaker.

The biostimulator transport system can include a valve bypass tool that can lock to an access introducer, and thus, can connect the biostimulator transport system to the access introducer. The valve bypass tool can be slidably mounted on the protective sheath. More particularly, an annular seal of the valve bypass tool, which can be mounted between a tool cap and a tool body of the valve bypass tool, can be in sliding contact with the protective sheath. Accordingly, the valve bypass tool can slide over, and seal against, the protective sheath of the biostimulator transport system.

In an embodiment, the valve bypass tool includes a bypass sheath having a tubular wall that can insert into the access introducer. The bypass sheath surrounds a bypass lumen, which can receive the protective sheath when the valve bypass tool is mounted on the protective sheath. More particularly, the tubular sheath can slide over the leadless pacemaker and the protective sheath. The bypass sheath may be metallic, e.g., may be formed from a thin-walled metal tubing. By contrast, the tool body can be polymeric, and thus, may be overmolded onto the tubular wall. The metallic tubing can be thin and rigid, and thus, the bypass sheath can be sufficiently strong to insert into a proximal opening of an access introducer without buckling, and sufficiently thin to allow the passage of the leadless pacemaker and the protective sheath though the bypass sheath into the access introducer.

In an embodiment, the valve bypass tool can lock to the access introducer to resist back out of the valve bypass tool when the leadless pacemaker and the protective sheath are inserted into the access introducer. The valve bypass tool can include a locking tab that extends radially outward from the tool body of the valve bypass tool. The locking tab can lock the tool body to the access introducer. For example, the locking tab can have a detent extending from a tab face of the locking tab. The valve bypass tool can be twisted into a locked configuration when the bypass sheath is inserted into the access introducer to engage the detent with a corresponding recess of the access introducer. When the detent engages the recess, the valve bypass tool is secured to the access introducer and resists back out. While secured, the leadless pacemaker and the protective sheath can be advanced through the bypass sheath and the access introducer into a patient.

The above summary does not include an exhaustive list of all aspects of the present invention. It is contemplated that the invention includes all devices, systems, and methods that can be practiced from all suitable combinations of the various aspects summarized above, as well as those disclosed in the Detailed Description below and particularly pointed out in the claims filed with the application. Such combinations have particular advantages not specifically recited in the above summary.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 17 is a flowchart of a method of locking a valve bypass tool to an access introducer, in accordance with an embodiment.

DETAILED DESCRIPTION

Figure 1:
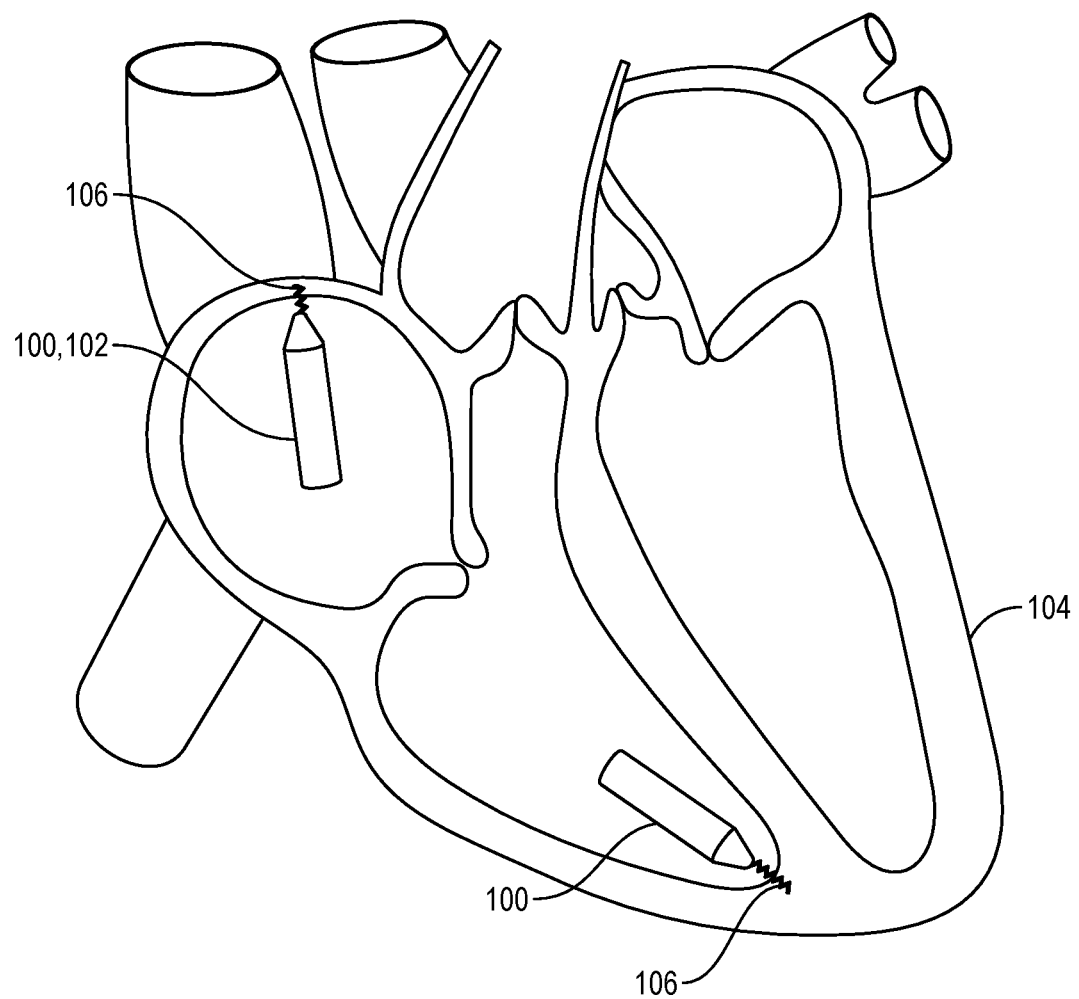
FIG. 1 is a diagrammatic medial-lateral cross section of a patient heart illustrating an example implantation of biostimulators in the patient heart, in accordance with an embodiment.

Embodiments describe a valve bypass tool and a biostimulator transport system, e.g., a catheter-based system for delivery or retrieval of a leadless pacemaker, having such a valve bypass tool. The valve bypass tool can mate to an access introducer to allow a biostimulator to be introduced through the valve bypass tool and the access introducer into a patient, to pace cardiac tissue. The biostimulator, however, may be used in other applications, such as deep brain stimulation. Thus, reference to the biostimulator as being a cardiac pacemaker is not limiting.

In various embodiments, description is made with reference to the figures. However, certain embodiments may be practiced without one or more of these specific details, or in combination with other known methods and configurations. In the following description, numerous specific details are set forth, such as specific configurations, dimensions, and processes, in order to provide a thorough understanding of the embodiments. In other instances, well-known processes and manufacturing techniques have not been described in particular detail in order to not unnecessarily obscure the description. Reference throughout this specification to "one embodiment," "an embodiment," or the like, means that a particular feature, structure, configuration, or characteristic described is included in at least one embodiment. Thus, the appearance of the phrase "one embodiment," "an embodiment," or the like, in various places throughout this specification are not necessarily referring to the same embodiment. Furthermore, the particular features, structures, configurations, or characteristics may be combined in any suitable manner in one or more embodiments.

The use of relative terms throughout the description may denote a relative position or direction. For example, "distal" may indicate a first direction along a longitudinal axis of a valve bypass tool. Similarly, "proximal" may indicate a second direction opposite to the first direction. Such terms are provided to establish relative frames of reference, however, and are not intended to limit the use or orientation of a biostimulator transport system to a specific configuration described in the various embodiments below.

In an aspect, a valve bypass tool, and a biostimulator transport system having such a valve bypass tool, is provided. The valve bypass tool includes several features to improve the interoperability of the valve bypass tool with an access introducer. The valve bypass tool can include a coupling, such as a modified Storz-type coupling, to engage and lock onto the access introducer and to reduce a likelihood that the valve bypass tool will back out of a hemostasis valve of the access introducer. The valve bypass tool can include a metallic, e.g., stainless steel, tool sheath that has a rigid and thin wall. The tool sheath can insert into the hemostasis valve without being crushed while providing a conduit for a protective sheath of the biostimulator transport system to be passed through. The valve bypass tool can be irreversibly and/or securely mounted on the protective sheath of the biostimulator transport system. More particularly, the valve bypass tool can be assembled onto the catheter components of the biostimulator transport system during manufacturing, and the valve bypass tool can include a tool cap that resists removal from the catheter components during use. The valve bypass tool can include push tabs that extend radially to allow a user to securely grip the valve bypass tool to exert greater axial and rotational force on the valve bypass tool during use. For example, the user can press on the push tabs to insert the tool sheath into the access introducer and to lock the coupling of the valve bypass tool to a mating coupling of the access introducer.

Referring to FIG. 1, a diagrammatic medial-lateral cross section of a patient heart illustrating an example implantation of biostimulator in the patient heart is shown in accordance with an embodiment. A cardiac pacing system includes one or more biostimulator 100. The biostimulator 100 can be implanted in the patient heart 104, and can be leadless, and thus may be leadless cardiac pacemaker 102. Each biostimulator 100 can be placed in a cardiac chamber, such as a right atrium and/or right ventricle of the patient heart 104, or attached to an inside or outside of the cardiac chamber. Attachment of the biostimulator 100 to the cardiac tissue can be accomplished via one or more fixation elements 106, such as helical anchors. In a particular embodiment, the leadless pacemaker can use two or more electrodes located on or within a housing of the leadless pacemaker for pacing the cardiac chamber upon receiving a triggering signal from internal circuitry and/or from at least one other device within the body.

Figures 2A, 2B:
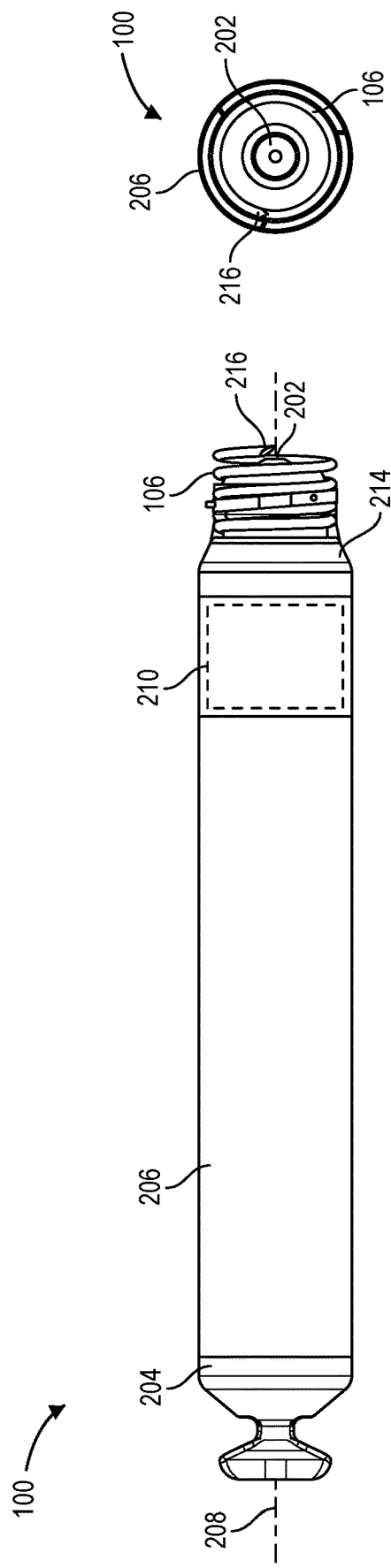
FIGS. 2A-2B are, respectively, side and end views of a biostimulator, in accordance with an embodiment.

Referring to FIG. 2A, a side view of a biostimulator is shown in accordance with an embodiment. The biostimulator 100 can be a leadless cardiac pacemaker 102 that can perform cardiac pacing and that has many of the advantages of conventional cardiac pacemakers while extending performance, functionality, and operating characteristics. The biostimulator 100 can have two or more electrodes, e.g., a distal electrode 202 and a proximal electrode 204, located within, on, or near a housing 206 of the biostimulator 100. In an embodiment, one or more of the fixation elements 106 forms a portion of the distal electrode 202. The electrodes can deliver pacing pulses to muscle of the cardiac chamber, and optionally, can sense electrical activity from the muscle. The electrodes may also communicate bidirectionally with at least one other device within or outside the body.

In an embodiment, the housing 206 has a longitudinal axis 208, and the distal electrode 202 can be a distal pacing electrode mounted on the housing 206 along the longitudinal axis 208. The housing 206 can contain a primary battery to provide power for pacing, sensing, and communication, which may include, for example, bidirectional communication. The housing 206 can optionally contain an electronics compartment 210 to hold circuitry adapted for different functionality. For example, the electronics compartment 210 can contain circuits for sensing cardiac activity from the electrodes, circuits for receiving information from at least one other device via the electrodes, circuits for generating pacing pulses for delivery via the electrodes, or other circuitry. The electronics compartment 210 may contain circuits for transmitting information to at least one other device via the electrodes and can optionally contain circuits for monitoring device health. The circuit of the biostimulator 100 can control these operations in a predetermined manner. In some implementations of a cardiac pacing system, cardiac pacing is provided without a pulse generator located in the pectoral region or abdomen, without an electrode-lead separate from the pulse generator, without a communication coil or antenna, and without an additional requirement of battery power for transmitted communication.

Leadless pacemakers or other leadless biostimulators 100 can be fixed to an intracardial implant site by one or more actively engaging mechanisms or fixation mechanisms, such as a screw or helical member that screws into the myocardium. In an embodiment, the biostimulator 100 includes the fixation element 106 coupled to the housing 206. The fixation element 106 can be a helical element to screw into target tissue. More particularly, the fixation element 106 can extend helically from a flange 214 of the biostimulator 100, which is mounted on the housing 206, to a distal tip at a helix distal end 216.

Referring to FIG. 2B, an end view of a biostimulator is shown in accordance with an embodiment. The helix distal end 216 can be located distal to the distal electrode 202 (a centrally located electrode). Accordingly, when the biostimulator 100 contacts the target tissue, the distal tip can pierce the tissue and the housing 206 can be rotated to screw the fixation element 106 into the target tissue to pull the distal electrode 202 into contact with the tissue. By contrast, the housing 206 can be rotated to unscrew the fixation element 106 from the target tissue to retrieve the biostimulator 100.

Leadless pacemakers or other leadless biostimulator 100 can be delivered to and retrieved from a patient using a transport system, as described below. In some implementations, the transport system is a delivery system for delivering the leadless pacemaker to the target tissue. In some implementations, the transport system is a retrieval system for retrieving the leadless pacemaker from the target tissue.

Figure 3A:
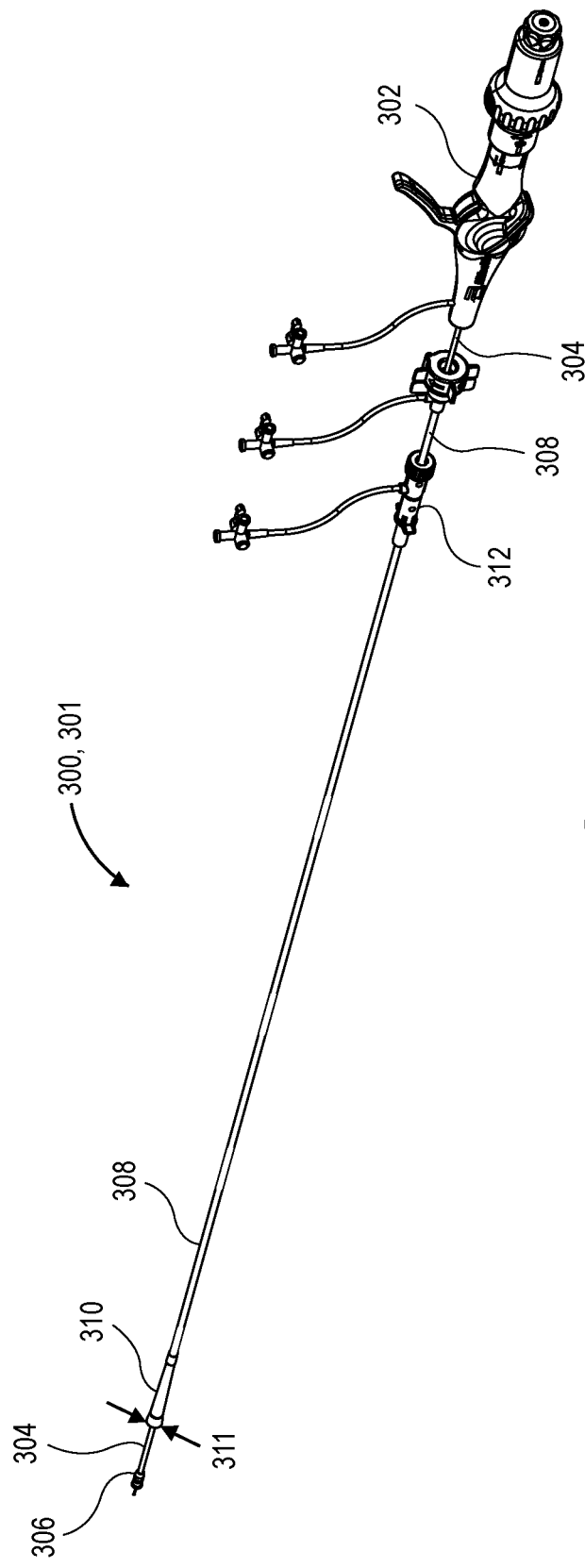
FIGS. 3A-3B are various views of a biostimulator delivery system, in accordance with an embodiment.

Referring to FIG. 3A, a perspective view of a biostimulator transport system is shown in accordance with an embodiment. A biostimulator transport system 300 may be used for delivery and/or retrieval of the biostimulator 100, e.g., a leadless pacemaker, into or from a patient. As shown in FIG. 3A, the biostimulator transport system can be a biostimulator delivery system 301 used for delivery of the biostimulator 100 into a patient. The biostimulator transport system 300 can include a handle 302, and an elongated catheter 304 extending distally from the handle 302 to a distal catheter end 306. The elongated catheter 304 can be a deflectable catheter, and an operator can use the handle 302 to steer the distal catheter end 306 in the patient. In an embodiment, the biostimulator transport system 300 includes a protective sheath 308 mounted on the elongated catheter 304. The protective sheath 308 can be slidably disposed on the elongated catheter 304. The protective sheath 308 can include an atraumatic end 310, e.g., a soft, funnel-shaped distal portion, that can slide distally over the distal catheter end 306 of the elongated catheter 304 and/or the biostimulator 100 (not shown). The atraumatic end 310 can have an outer dimension 311, which may be larger than a proximal portion of the protective sheath 308. For example, the atraumatic end 310 may flare in a distal direction to a funnel opening having the outer dimension 311, which is larger than a region of the protective sheath 308 supporting a valve bypass tool 312. The biostimulator transport system 300 can include the valve bypass tool 312 mounted on the protective sheath 308. The valve bypass tool 312 can be slidably disposed on the protective sheath 308 such that a distal portion of the valve bypass tool 312 can slide distally over the distal end of the elongated catheter 304 and/or the distal portion of the protective sheath 308. More particularly, the valve bypass tool 312 can be inserted into an access introducer to gain access to the patient vasculature, and after access is established, the distal portion of the protective sheath 308 and/or the distal end of the elongated catheter 304 can be advanced through the valve bypass tool 312 into the patient.

The distal catheter end 306 of the elongated catheter 304 may be selectively connectable to the biostimulator 100. More particularly, the biostimulator 100 can be mounted on the distal catheter end 306 of the elongated catheter 304. The biostimulator 100 can be protected by the atraumatic end 310 of the protective sheath 308 during delivery and/or retrieval of the biostimulator 100 from the patient. Accordingly, the biostimulator 100 can be advanced into the patient along with the distal catheter end 306.

The elongated catheter 304 of the biostimulator delivery system 301 can include a torque shaft that is torqueable and can be used to rotate the biostimulator 100 in a first direction, e.g., clockwise. Rotating the biostimulator 100 in a first direction when the fixation element 106 is in contact with the heart tissue can cause the fixation element 106 to screw into the heart tissue and affix the biostimulator 100 to the heart tissue. By contrast, rotating the biostimulator 100 in a second direction opposite to the first direction when the fixation element 106 is affixed to the heart tissue can cause the fixation element 106 to unscrew from the heart tissue.

Figure 3B:
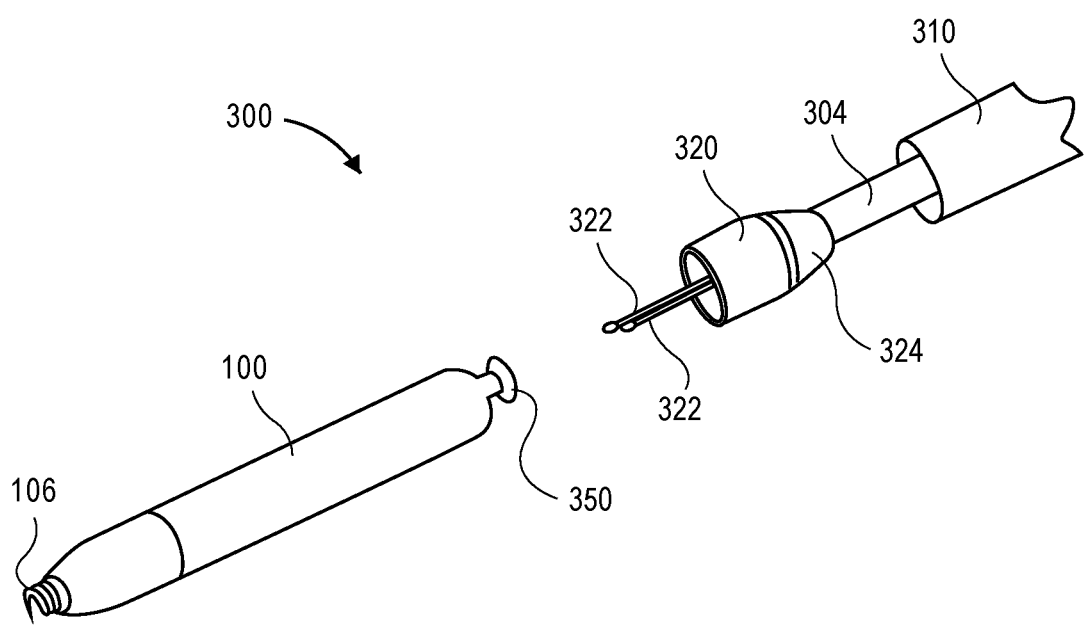

Referring to FIG. 3B, a perspective view of a distal portion of a biostimulator delivery system prior to attaching to a biostimulator is shown in accordance with an embodiment. The view is a close-up view of one embodiment of a distal portion of the biostimulator transport system 300 shown in FIG. 3A, which is used for delivery of a leadless pacemaker. Accordingly, the delivery system can include features to engage the leadless pacemaker to allow carrying the leadless pacemaker to a target tissue site and screwing the biostimulator 100 into the target tissue.

The distal portion of the biostimulator delivery system 301 can include a docking cap 320 configured to allow docking of the leadless pacemaker with the biostimulator transport system 300 after engaging the pacemaker with one or more tethers 322. Each tether 322 can extend through the elongated catheter 304. A bearing housing 324 can be mounted on the distal catheter end 306. The hearing housing 324 can contain a bearing to support the docking cap 320 and to allow relative rotation between the docking cap 320 and the bearing housing 324 during torque transmission. More particularly, the bearing housing 324 can be mounted on the elongated catheter 304, and the docking cap 320 can be mounted on the torque shaft of the elongated catheter 304 (hidden within the elongated catheter 304). A user can transmit torque through the torque shaft via handle controls to rotate the docking cap 320 relative to the bearing housing 324. More particularly, the torque shaft can extend through the length of the catheter to a torque knob on the handle 302, or another rotatable portion of the handle 302, which is coupled to the torque shaft. Rotation or actuation of the torque knob rotates the torque shaft, thereby rotating the docking cap 320 at the end of the biostimulator delivery system 301. In some implementations, the docking cap 320 can include a keyed portion or interference feature so as to apply additional torque to the pacemaker 100 when rotating the biostimulator 100. The atraumatic end 310 of the protective sheath 308 can be positioned along the elongated catheter 304, and can be advanced or retracted to cover or expose the docking cap 320 and the leadless pacemaker.

In an embodiment, the tethers 322 of the biostimulator transport system 300 are configured to engage a docking feature on the biostimulator 100. The tethers 322 can include wires, shafts, tubes, cords, ropes, strings, or other similar structures that can extend throughout the elongated catheter 304. In some implementations, the tethers 322 include a shape memory material, such as nitinol. In other implementations, the tethers 322 include stainless steel wires or braids. The tethers 322 can include distal features, for example, features on the tethers 322 that protrude radially from the tether 322, such as humps, spheres, cylinders, rectangles, or other similar shapes extending outward from the tethers 322. Generally, the distal features have a cross-sectional diameter larger than the cross sectional diameter of the tethers 322. In one embodiment, the distal feature on a first tether 322 can be advanced further from the catheter than the distal feature on a second tether 322 such that, when the tethers 322 are pushed together, the distal feature on the second tether 322 rests against the first tether 322. This causes the combined cross sectional dimension of the distal feature and the tether to be less than if the distal features were lined up side by side.

When the tethers 322 and distal features are in the un-aligned configuration, the cross sectional diameter of the distal features is reduced since the distal features are not positioned side by side. The tether distal features can then be advanced in this un-aligned configuration through a hole (not shown) of an attachment feature 350 of the leadless pacemaker. In this implementation, the diameter of the hole can be sufficiently large enough to allow the distal features of the tethers 322 to pass when in the un-aligned configuration. Upon passing the distal features through the hole, the length of the tethers 322 can then be adjusted to align the distal features in the side-by-side configuration. When the distal features are positioned side-by-side, the combined cross-sectional diameter of the distal features becomes larger than the diameter of the hole, which essentially locks the tethers 322 and distal features in the attachment feature 350, and prevents the distal features from being able to pass proximally through the hole.

When the tethers 322 are locked to the biostimulator 100, the tethers 322 can be retracted to dock the biostimulator 100 to the docking cap 320. More particularly, the attachment feature 350 of the biostimulator 100 can be pulled into a docking cavity of the docking cap 320. The docking cap 320 of the delivery system can include a torque slot (not shown) sized and configured to mate with the attachment feature 350 of the biostimulator 100. It should be appreciated that the attachment feature 350 and the torque slot can include any number of shapes, such as square, rectangle, triangle, pentagon, hexagon, cross, "X", etc., so long as the attachment feature 350 fits within and can have rotational torque applied to it by the torque slot. When the attached feature is docked, the distal end of the biostimulator transport system 300 can be navigated through the patient to a delivery site. The torque slot can be rotated via rotation of the torque shaft to screw the biostimulator 100 into the cardiac tissue at the delivery site. The tethers 322 can be misaligned to release the biostimulator 100 from the biostimulator transport system 300 at the delivery site.

Figure 4A:
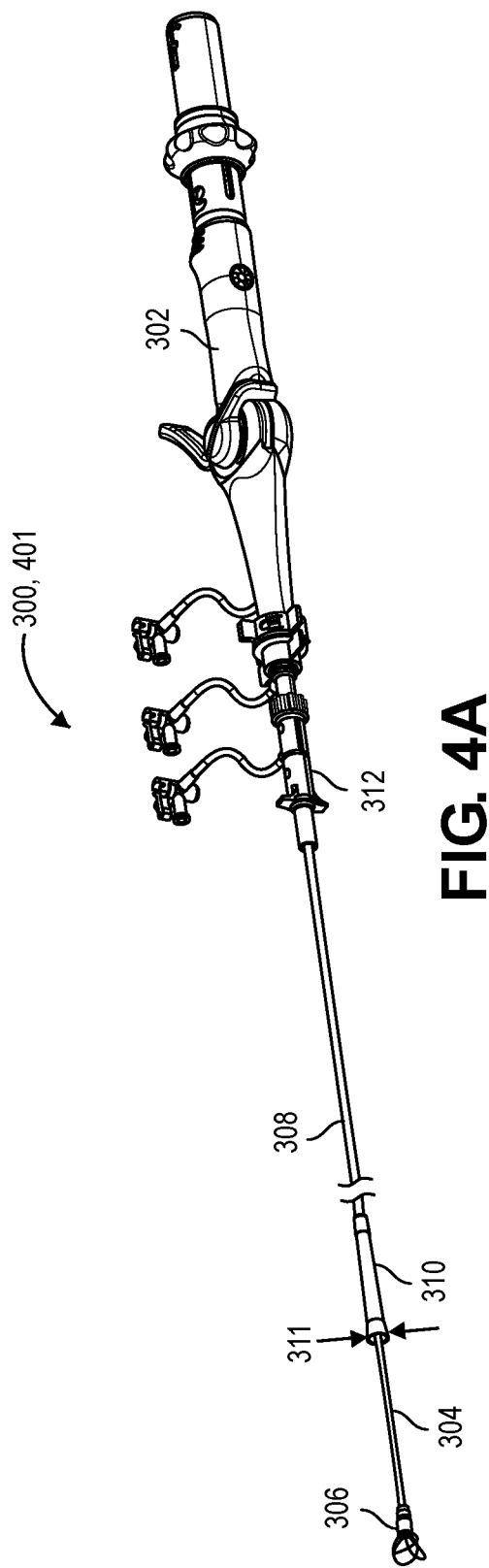
FIGS. 4A-4B are various views of a biostimulator retrieval system, in accordance with an embodiment.

Referring to FIG. 4A, a perspective view of a biostimulator retrieval system is shown in accordance with an embodiment. The biostimulator transport system 300 may be a biostimulator retrieval system 401. The biostimulator retrieval system 401 can be used to explain one or more biostimulator 100 from the atrium and/or the ventricle of the heart of the patient. Removal and retrieval of the biostimulator(s) 100 may be accomplished endocardially. For example, the torque shaft of the elongated catheter 304 can be rotated in a second direction, e.g., counterclockwise, to disengage the biostimulator 100 from the heart tissue. Accordingly, retrieval system 401 shown in FIG. 4 can have a structure similar to that shown and described with respect to the delivery system of FIG. 3 to retrieve the biostimulator 100 from a target anatomy.

Figure 4B:
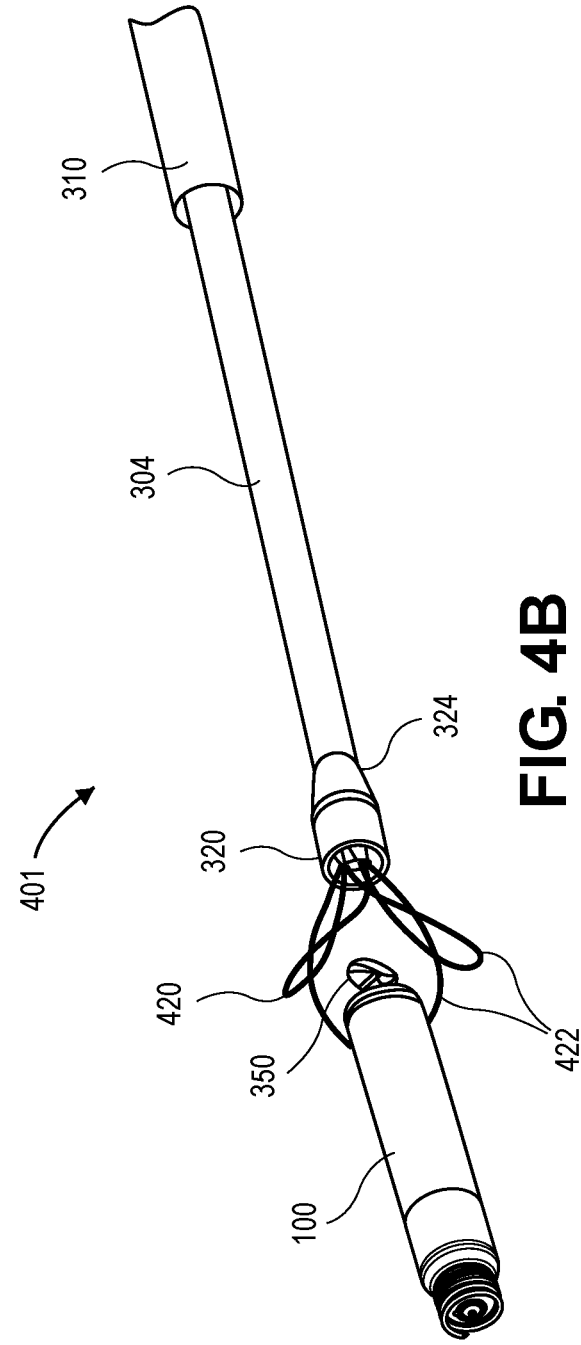

Referring to FIG. 4B, a perspective view of a distal portion of a biostimulator retrieval system prior to attaching to a biostimulator is shown in accordance with an embodiment. The distal portion of the biostimulator transport system 300 can include features to engage the leadless pacemaker to facilitate capturing and unscrewing the biostimulator 100 from the target tissue. More particularly, the biostimulator retrieval system 401 can include a snare 420 extending through the elongated catheter 304 to grasp a biostimulator 100 or other medical device. The snare 420 can include at least one snare loop 422, e.g., a wire loop, extending from the elongated catheter 304. As the snare 420 is advanced distally out of the biostimulator transport system 300 from the docking cap 320, the loop(s) 422 can expand in size to aid a user in positioning the snare 420 around or in proximity to the biostimulator 100 to be retrieved. In some implementations, as in FIG. 4B, the snare 420 can include multiple loops, such as three loops. However, any number of loops can be used as long as the elongated catheter 304 contains sufficient volume to accommodate the loops.

The distal portion of the retrieval catheter can include the docking cap 320 configured to allow docking of the leadless pacemaker with the biostimulator transport system 300 after engaging the pacemaker with the snare 420, and the bearing housing 324 that contains a bearing to support the docking cap 320 and to allow relative rotation between the docking cap 320 and the bearing housing 324 during torque transmission. A user can transmit torque through the torque shaft via handle 302 controls to rotate the docking cap 320 relative to the bearing housing 324. More particularly, the torque shall can extend through the length of the catheter to a torque knob on the handle 302, or another rotatable portion of the handle 302, which is coupled to the torque shaft. Rotation or actuation of the torque knob rotates the torque shaft, thereby rotating the docking cap 320 at the end of the retrieval catheter. The protective sheath 308 can be positioned along the elongated catheter 304, and can be advanced or retracted to cover or expose the docking cap 320 and the leadless pacemaker 100 with the atraumatic end 310.

During retrieval, the biostimulator transport system 300 can be navigated through the patient to the implant site. The snare 420 can be placed over the attachment feature 350, e.g., a handle 302 or hook feature on the biostimulator 100, and the loops of the snare 420 can be reduced in size, thereby grasping or locking onto the attachment feature 350 of the pacemaker. Following capture and locking of the snare 420 with the leadless pacemaker, the biostimulator 100 may be docked within the docking cap 320. More particularly, the attachment feature 350 of the biostimulator 100 can be pulled into a docking cavity of the docking cap 320. In some implementations, the docking cap 320 can include a key or interference feature configured to mate with and engage a corresponding key or feature on the pacemaker. In some implementations, the key or slot on the docking cap 320 can match a unique shape or feature of the attachment feature 350 of the pacemaker. Because the key or slot on or in the docking cap 320 can mate with and engage the key or slot on the pacemaker, the retrieval catheter can be configured to apply torque to the pacemaker to unscrew and remove the pacemaker from tissue.

Figure 5:
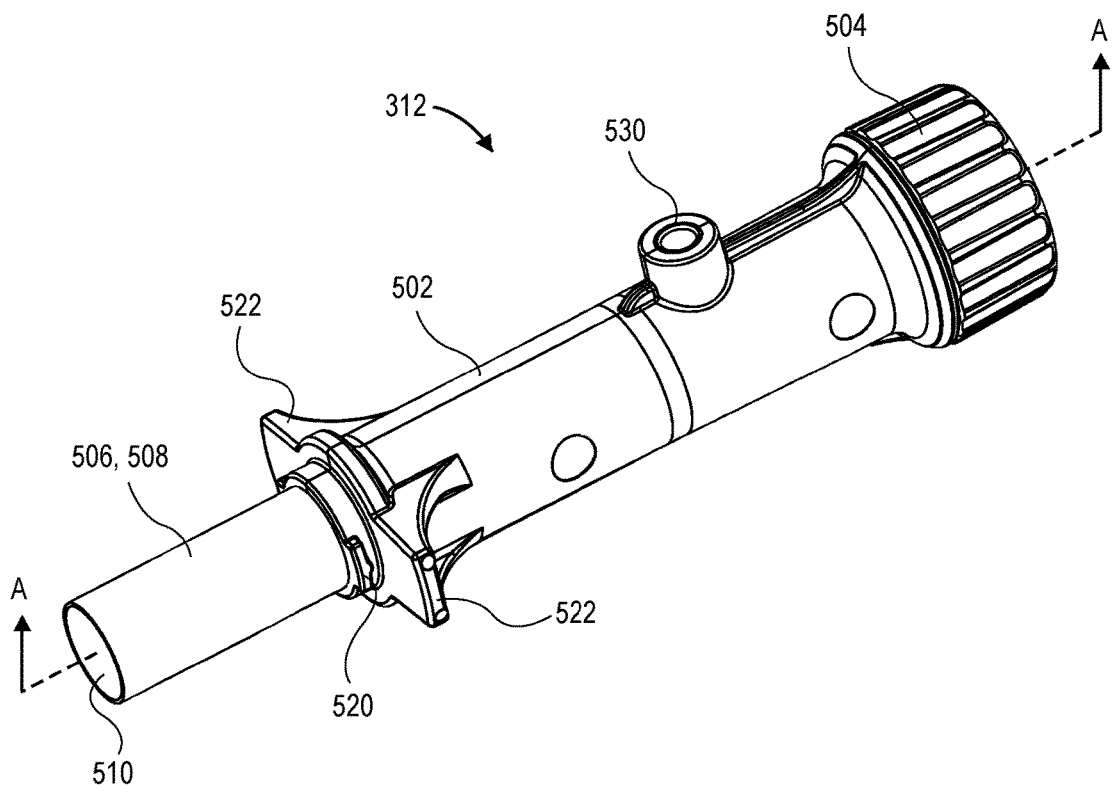
FIG. 5 is a proximal perspective view of a valve bypass tool, in accordance with an embodiment.

Referring to FIG. 5, a proximal perspective view of a valve bypass tool is shown in accordance with an embodiment. The valve bypass tool 312 can have a tool body 502, which the user can handle to advance, retract, and rotate the valve bypass tool 312 about the protective sheath 308. A tool cap 504 may be mounted on the tool body 502. For example, the tool cap 504 can be threadably or otherwise connected to the tool body 502. In an embodiment, the tool cap 504 is welded, e.g., ultrasonically welded, to the tool body 502. As described below, the tool cap 504 can retain a seal that is in sliding contact with the protective sheath 308, and seals a gap between an inner surface of the tool body 502 and an outer surface of the protective sheath 308 so as to prevent blood from leaking outward through the gap.

The valve bypass tool 312 can include a bypass sheath 506 extending distally from the tool body 502. The tool body 502 may be integrally formed with the bypass sheath 506. In an embodiment, however, the tool body 502 and the bypass sheath 506 are separate components. For example, the tool body 502 can be mounted on a tubular wall 508 of the bypass sheath 506.

The tubular wall 508 of the bypass sheath 506 can extend around a bypass lumen 510. In an embodiment, the tubular wall 508 is thin and strong to optimize the interoperability of the bypass sheath 506 with other components. For example, the bypass sheath 506 can have an outer diameter that is sized to reduce insertion forces into an access introducer, e.g., a 25 Fr access introducer. Similarly, the bypass sheath 506 can have an inner diameter, e.g., a cross-sectional dimension of the bypass lumen 510, that allows the biostimulator 100 and/or the protective sheath 308 to move smoothly through the bypass lumen 510. This duality of a minimum outer dimension and a maximum inner dimension can be achieved by the features of the tubular wall 508 described below.

In an embodiment, the tubular wall 508 is formed from a rigid material that can provide a thin wall and still prevent collapsing of the bypass sheath 506 when it is inserted into an access introducer. The rigid material can be a stiff polymer, such as nylon, e.g., nylon 8 or nylon 12, polyether ether ketone (PEEK), polyimide, etc. In an embodiment, the bypass sheath 506 is metallic. For example, the tubular wall 508 can be a stainless steel, e.g., 304 SST, tube having a thin wall. The stainless steel tubular wall 508 can provide superior rigidity and a stiffer sheath having a reduced wall thickness as compared to polymeric bypass sheath materials.

Given that the bypass sheath 506 can be formed from a material suited to the purpose described above, the tool body 502 may be formed from a different material than the bypass sheath 506. For example, the tool body 502 may be polymeric, and may be formed from a different polymer than the rigid polymers (or the rigid metal) described above. In an embodiment, the polymeric tool body 502 is overmolded onto the metallic bypass sheath 506 in an insert molding process to form a secure bond between the dissimilar materials. More particularly, a distal end of the tool body 502 can be molded onto a proximal end of the bypass sheath 506.

In addition to having the bypass sheath 506 that eases insertion into a hemostasis valve of an access introducer, the valve bypass tool 312 can also include a coupling to lock onto the access introducer. The coupling can resist back out of the valve bypass tool 312 from the access introducer. The coupling can engage the access introducer, as described below. In an embodiment, the coupling includes one or more locking tabs 520 that extend radially outward from the tool body 502. For example, the valve bypass tool 312 can include several locking tabs 520 extending radially outward from a distal lip of the tool body 502. The locking tabs 520 can be evenly distributed along the distal lip about a longitudinal axis of the valve bypass tool 312. More particularly, when the valve bypass tool 312 has two locking tabs 520, each locking tabs 520 can be located at the distal lip and spaced from the other locking tabs 520 by 180 degrees about the longitudinal axis. The structure of the locking tab(s) 520 is described further below, however, it is noted here that the locking tab(s) 520 are couplings that provide a strong lock between the valve bypass tool 312 and an access introducer during an implantation or explanation procedure. For example, the looking tabs 520 can be male Storz-type couplings that engage female Storz-type couplings of the access introducer.

To aid in inserting the bypass sheath 506 into the access introducer, and to locking the locking tabs 520 into corresponding couplings of the access introducer, the valve bypass tool 312 can include one or more push tabs 522. Each push tab 522 can extend radially outward from the tool body 502 to provide a fin or flange structure that a user can push forward against. More particularly, the user can grip the tool body 502 behind the push tab(s) 522 and push forward on the push tab(s) 522 to drive the bypass sheath 506 into the access introducer. When the bypass sheath 506 is inserted into the access introducer, the user can then twist the valve bypass tool 312, e.g., by pressing sideways on the push tabs 522 to rotate the tool body 502, to engage the locking tabs 520 of the valve bypass tool 312 within the access introducer. For example, the bypass tool can be twisted 90 degrees clockwise to engage and/or lock the couplings of the valve bypass tool 312 and the access introducer. A structure of the push tabs 522 as described in more detail below, however, it will be appreciated that the push tabs 522 can include a structure that extends radially outward far enough for the user to easily press against a rear surface of the tabs. By way of example, the push tab 522 can be an annular disk-like structure extending radially outward from the tool body 502 and extending entirely around the tool body 502. In an embodiment, the push tabs 522 include two fin-like structures extending radially outward from the tool body 502 on diametrically opposed sides of the tool body 502, as shown in FIG. 5.

As shown above in FIGS. 3-4, each of the catheter components of the biostimulator transport system 300 can include a flush port extending respectively therefrom. More particularly, the flush ports can be used to flush saline or other fluids through the respective catheter component. In an embodiment, the flush port of the valve bypass tool 312 includes a luer-type fitting connected to a flush line. The flush line extends between the fitting and a sideport 530 on the tool body 502. The sideport 530 includes a flange 214 extending radially outward from an outer surface of the tool body 502, and a hole extending through the flange 214 from a surrounding environment into a body lumen 612 (FIG. 6) within the tool body 502. The flush line can be received within the sideport 530 hole, and sealed to the flange 214 by a hermetic joint, e.g., an adhesive bond. Accordingly, saline can be flushed through the fitting, the flush line, and the sideport 530 into the body lumen 612. The saline can travel distally through a gap between the tool body 502 and the protective sheath 308, and out of the bypass lumen 510 when the bypass sheath 506 is inserted into a hemostasis valve of the access introducer.

Figure 6:
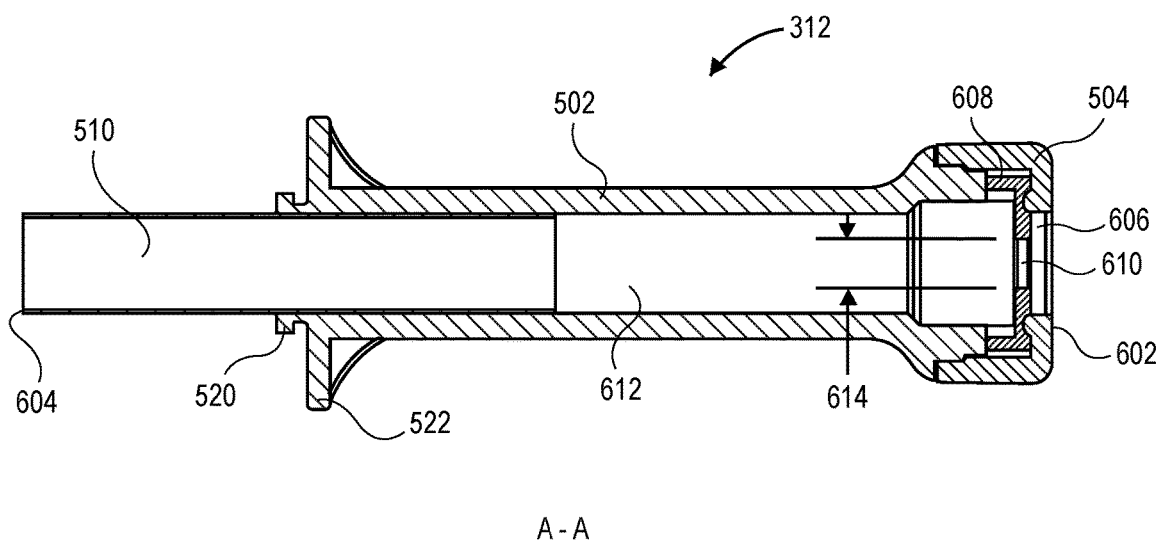
FIG. 6 is a cross-sectional view, taken about line A-A of FIG. 5, of a bypass tool, in accordance with an embodiment.

Referring to FIG. 6, a cross-sectional view, taken about line A-A of FIG. 5, of a bypass tool is shown in accordance with an embodiment. The valve bypass tool 312 may be permanently or semi-permanently mounted on the protective sheath 308 of the biostimulator transport system 300. A permanently mounted valve bypass tool 312 may not be removed from the system without damaging some component of the system. A semi-permanently mounted valve bypass tool 312 can be removed from the system with sufficient force applied by the user, however, the valve bypass tool 312 can include features that resist such removal, as described below. It is contemplated that insertion of the leadless pacemaker or the protective sheath 308 through the access introducer without the use of the valve bypass tool 312 could lead to device damage, and thus, features to resist removal of the valve bypass tool 312 from the protective sheath 308 can reduce a likelihood of such failures.

To facilitate mounting on the protective sheath 308, the valve bypass tool 312 includes a central lumen extending from a proximal tool end 602 to a distal tool end 604. Each component of the valve bypass tool 312 can have a respective lumen, and the lumens can combine to form the central lumen. For example, the tool cap 504, which may be mounted on the tool body 502, can include a cap lumen 606 extending from a proximal face of the cap at the proximal tool end 602 to an internal face of the cap that faces distally toward the tool body 502. In an embodiment, the valve bypass tool 312 includes an annular seal 608 mounted on, or otherwise coupled to, the tool body 502. For example, the annular seal 608 can be between the tool cap 504 and the tool body 502. The annular seal 606 can include a seal lumen 610 that extends through the annular seal 608 from the cap lumen 606 to a body lumen 612 of the tool body 502. Accordingly, the cap lumen 606, the seal lumen 610, and the body lumen 612 can be aligned along the longitudinal axis of the valve bypass tool 312. More particularly, the cap lumen 606, the seal lumen 610, the body lumen 612, and the bypass lumen 510 can combine to form the central lumen of the valve bypass tool 312 through which the protective sheath 308 may be inserted.

When the valve bypass tool 312 is mounted on the protective sheath 306 with the protective sheath 308 received in the central lumen, the annular seal 608 can be in sliding contact with an outer surface of the protective sheath 308. More particularly, the seal lumen 610 can have a seal lumen dimension 614, e.g., an inner diameter, that is less than an outer diameter of the protective sheath 308. The annular seal 608 can be a gasket, an o-ring, a washer, etc. For example, the seal can be an injection molded silicone component, that includes a flexible body having an inner profile and an outer profile. The seal can be pressed between a distal face of the tool cap 504 and a proximal end of the tool body 502. More particularly, the seal can have an outer surface that is received in a gap between the distal face of the tool cap 504 and the proximal end of the tool body 502 to retain the gasket when the protective sheath 308 slides within the seal lumen 610. Thus, when the protective sheath 308 is inserted through the seal lumen 610, the annular seal 608 can distend to accept the larger sheath body. When the seal distends, a surface of the seal can press against the protective sheath 308 to form a hemostatic seal between the valve bypass tool 312 and the protective sheath 308. The hemostatic seal can move along the protective sheath 308 as the sheath is slid back and forth within the valve bypass tool 312 during an interventional procedure.

Figure 7:
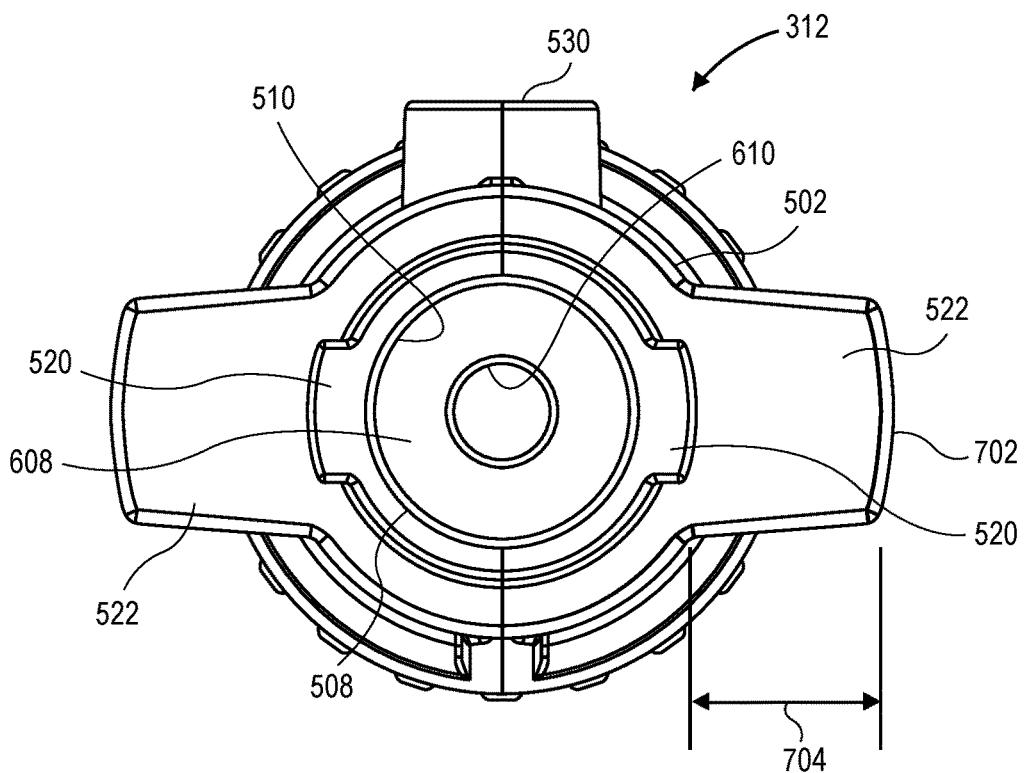
FIG. 7 is a distal end view of a bypass tool, in accordance with an embodiment.

Referring to FIG. 7, a distal end view of a bypass tool is shown in accordance with an embodiment. In the end view, it is evident that the inner diameter of the seal lumen 610 is smaller than an inner diameter of the bypass lumen 510, allowing the annular seal 608 to seal against the protective sheath 308 when the protective sheath 308 is received within the tubular wall 508 of the bypass sheath 506.

In an embodiment, the valve bypass tool 312 includes the one or more push tabs 522 extending radially outward from the tool body 502 to an outer tab face 702. The outer tab face 702 can be an outer surface of the push tab 522 that faces radially outward away from the longitudinal axis of the valve bypass tool 312. For example, the valve bypass tool 312 can include a disk that extends around the entire surface of the tool body 502 and has a radial width between the tool body 502 and the outer tab face 702. In an embodiment, the valve bypass tool 312 includes several push tabs 522 distributed about the longitudinal axis. The push tabs 522 can be wings or fins extending symmetrically from opposite sides of the tool body 502. For example, as shown in FIG. 7, a first push tab 522 can extend radially rightward from the longitudinal axis, and a second push tab 522 can extend radially leftward from the longitudinal axis. Each push tab 522 can be sized to facilitate a user pushing or twisting the valve bypass tool 312. In an embodiment, a radial dimension 704 between the tool body 502 and the outer tab face 702 can be large enough that the fingertips of the user can easily press against a rear surface of the tabs.

Figure 8:
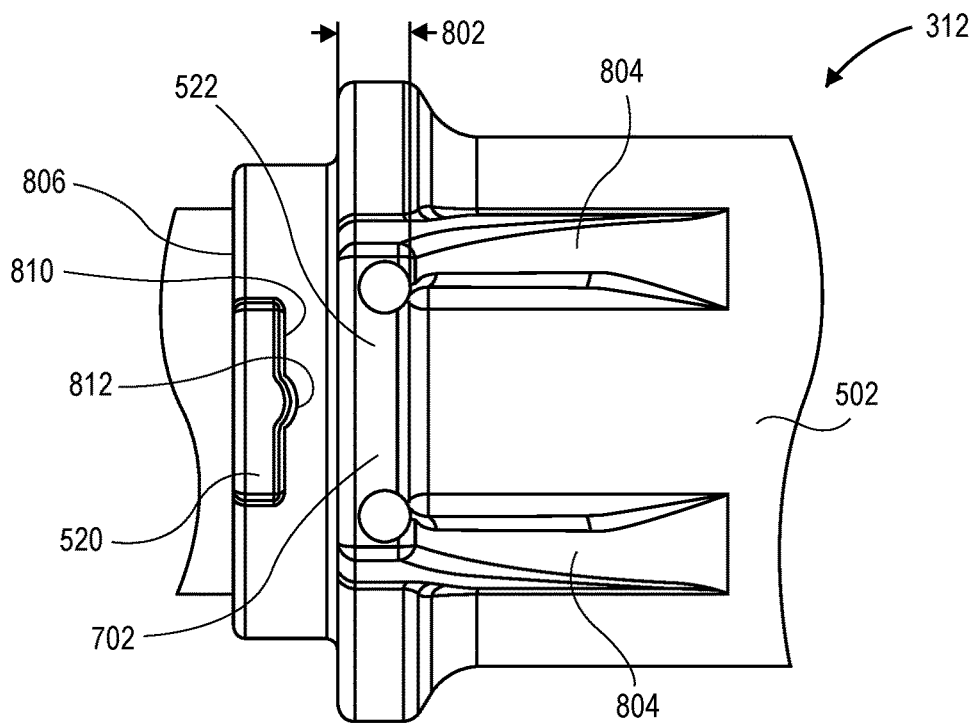
FIG. 8 is a partial side view of a bypass tool, in accordance with an embodiment.

Referring to FIG. 8, a partial side view of a bypass tool is shown in accordance with an embodiment. It may be important to minimize an overall length of the valve bypass tool 312, and thus, a longitudinal length of the push tabs 522 may be minimized. More particularly, a longitudinal dimension 802 of the outer tab face 702 may be minimized. In an embodiment, the radial dimension 704 of the push tab 522 is greater than a longitudinal dimension 802 of the outer tab face 702. For example, the radial dimension 704 of the push tab 522 may be at least twice the longitudinal dimension 802 of the push tab 522. This ratio of width to thickness provides an ergonomic feature to push forward on the valve bypass tool 312 and drive the bypass sheath 506 into an access introducer.

The valve bypass tool 312 can include structural features to reinforce the push tabs 522 despite the tabs being wider than they are long. In an embodiment, the valve bypass tool 312 includes one or more ribs 804 extending longitudinally from the push tab 522 to the tool body 502. For example, the valve bypass tool 312 can have several ribs 804. Each rib 804 can connect to the push tab 522 at a lateral edge of the outer tab face 702. More particularly, a first rib 804 can connect to the push tab 522 at a first lateral edge circumferentially offset from a second lateral edge of the outer tab face 702. A second rib 804 can attach to the second lateral edge. Each of the ribs 804 can have a radial width at the lateral edges that are the same as the radial dimension 704 of push tab 522. The ribs 804 can extend longitudinally rearward from the push tab 522 to the tool body 502. As the ribs 804 extend longitudinally rearward, the radial width of the ribs 804 can decrease to transition the rib 804 from the push tab 522 to the tool body 502. The ribbed transition between the push tab 522 and the tool body 502 can reinforce the push tab 522 such that the push tab 522 does not flex when pressed by the user. Furthermore, the ribs 804 can provide an additional surface for the user to grip in order to apply a rotational torque that twists the valve bypass tool 312. The user can twist the valve bypass tool 312 during insertion into the hemostasis valve of the access introducer, and to lock the coupling of the valve bypass tool 312 to the coupling of the access introducer.

The coupling mechanism of the valve bypass tool 312 can include several, e.g., two, locking tabs 520 or key features on a distal end of the tool body 502, e.g., at a distal lip 806. As shown in FIG. 7, the locking tabs 520 can have respective radial widths between the distal lip 806 and respective outward faces. Similar to the push tabs 522, the locking tabs 520 can be symmetrically disposed about the longitudinal axis, e.g., a first locking tab 520 can extend rightward from the tool body 502 and a second locking tab 520 can extend leftward from the tool body 502. The outward face of the rightward extending locking tabs 520 of FIG. 7 is shown in FIG. 8.

The locking tabs 520 can have a distal face facing in a distal direction of the longitudinal axis, and a proximal face facing in a proximal direction. One or more of the proximal face or the distal face can be a tab face 810 that engages a corresponding face of the access introducer when the valve bypass tool 312 is locked to the access introducer. The mechanism by which the locking tabs 520 engage the access introducer may be a Storz-lock type coupling that uses interlocking hooks and flanges to join the valve bypass tool 312 to the access introducer. It is noted, however, that rather than having both male and female coupling features, the valve bypass tool 312 and the access introducer may have only one or the other. For example, the valve bypass tool 312 may have a male coupling and the access introducer may have the female coupling, or vice versa. Other couplings having features that interfere to resist axial separation may also be incorporated as a locking coupling to connect the valve bypass tool 312 to the access introducer.

The locking tabs 520 can include a feature that increases friction between one or more of the surfaces of the locking tabs 520 and one or more surfaces of the access introducer when the valve bypass tool 312 is locked to the access introducer. In an embodiment, the locking tabs 520 includes a detent 812 extending from the tab face 810. As described below, a female coupling of the access introducer can include a groove that receives the locking tabs 520. The detent 812 can have a proximalmost location that is more proximal to a proximalmost location of the tab face 810.

Accordingly, when the locking tabs 520 is received in the groove, the detent 812 can slide along a surface of the groove. The detent 812 can bias the locking tabs 520 in a forward direction such that an opposing surface, e.g., a distal face of the locking tabs 520, presses against a corresponding surface of the access introducer. More particularly, friction between the access introducer and the valve bypass tool 312 can be increased to reduce a likelihood that the valve bypass tool 312 will back out of the access introducer.

In addition to increasing friction between the locking tabs 520 and the access introducer, the detent 812 can also be a nub that fits into a corresponding recess (FIG. 16) or dimple in the access introducer. As described below, when the detent 812 mates to the recess, the detent 812 can interfere with a corresponding surface of the access introducer, and thus, can resist unlocking of the valve bypass tool 312 from the access introducer.

Figure 9:
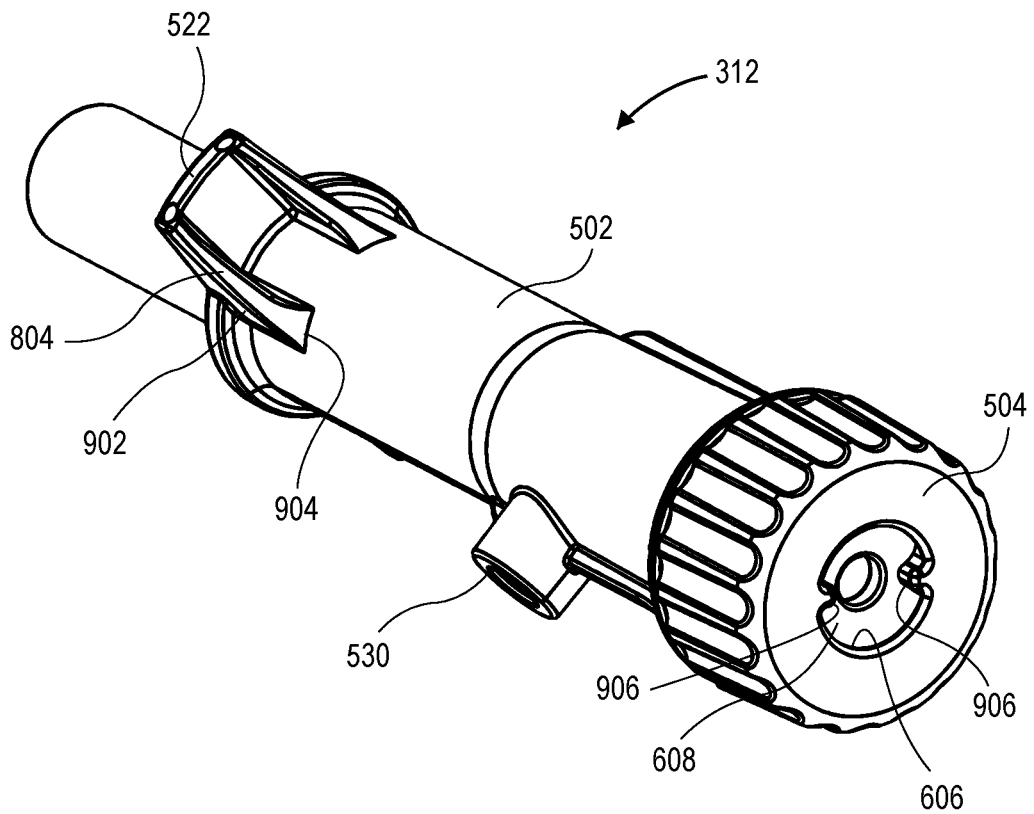
FIG. 9 is a distal perspective view of a valve bypass tool, in accordance with an embodiment.

Referring to FIG. 9, a distal perspective view of a valve bypass tool is shown in accordance with an embodiment. In the distal perspective view (viewing the valve bypass tool 312 in the distal direction) certain features of the valve bypass tool 312 are more apparent. For example, the transition of the ribs 804 from the push tabs 522 to the tool body 502 can be viewed more easily. More particularly, it is seen that each rib 804 can include a sidewall 902 that extends from the push tab 522 to a proximalmost transition point 904 of the rib 804. A radial dimension 704 of the sidewall 902 can diminish in the proximal direction such that the radial dimension 704 decreases at each point in the distal direction along the rib 804. The tapering rib 804 provides a smooth transition into the tool body 502.

It is also apparent that, when viewed in the distal direction, the tool cap 504 has the cap lumen 606, and the annular seal 608 is exposed to the surrounding environment through the cap lumen 606. The mismatch in sizing allows the protective sheath 308 to be inserted through the cap lumen 606 and to distend the annular seal 608. In an embodiment, the tool cap 504 includes one or more catch features that resists removal from the protective sheath 308. For example, the catch features can include a prong 906 that acts as a block or stop to catch on the atraumatic end 310 of the protective sheath 308 in the event that the valve bypass tool 312 slides fully forward on the protective sheath 308.

Figure 10:
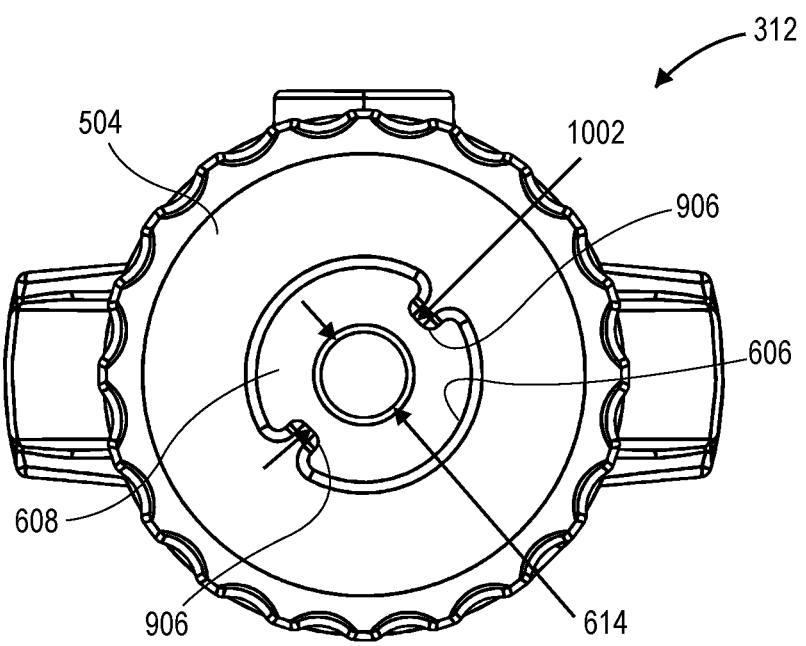
FIG. 10 is a proximal end view of a valve bypass tool, in accordance with an embodiment.

Referring to FIG. 10, a proximal end view of a valve bypass tool is shown in accordance with an embodiment. Expansion or distention of the annular seal 608 when the valve bypass tool 312 is mounted on the protective sheath 308 may be allowed by a difference in radial dimensions of the seal and the cap features. In an embodiment, the cap lumen 606 has a minimum cap lumen dimension 1002 that is larger than the seal lumen dimension 614 of the annular seal 608. The seal lumen dimension 614 can be a diameter of the through-hole extending longitudinally through the flexible seal component. Accordingly, the seal lumen dimension 614 can increase when the dimension of the protective sheath 308 sliding within the annular seal 608 increases, e.g., when the flared profile of the atraumatic end 310 is retracted proximally through the annular seal 608.

Whereas the seal lumen dimension 614 may increase as the atraumatic end 310 is retracted into the tool cap 504, the minimum cap lumen dimension 1002 may not increase. More particularly, the minimum cap lumen dimension 1002 may be a transverse width between several prongs 906 of the tool cap 504, and the prongs 906 may be rigid structures that do not flex when pressed radially outward. To resist dislodgment of the valve bypass tool 312 from the protective sheath 308, the minimum cap lumen dimension 1002 of the cap lumen 606 may be less than the outer dimension 311 of the atraumatic end 310 of the protective sheath 308. Accordingly, when the flared profile of the atraumatic end 310 is pulled into the cap lumen 606, the prongs 906 or other catch features of the tool cap 504 can catch on the outer surface of the protective sheath 308 and prevent removal of the protective sheath 308 from the valve bypass tool 312. The interference between the tool cap 504 and the atraumatic end 310 may be configured to allow a user to dislodge the protective sheath 308 by applying sufficient proximal loading to the protective sheath 308. By contrast, the interference may be configured such that pulling the protective sheath 308 proximally from the tool cap 504 cannot be accomplished without damaging some component of the biostimulator transport system 300, potentially preventing operation of the biostimulator transport system 300 without an intact bypass tool.

Figure 11:
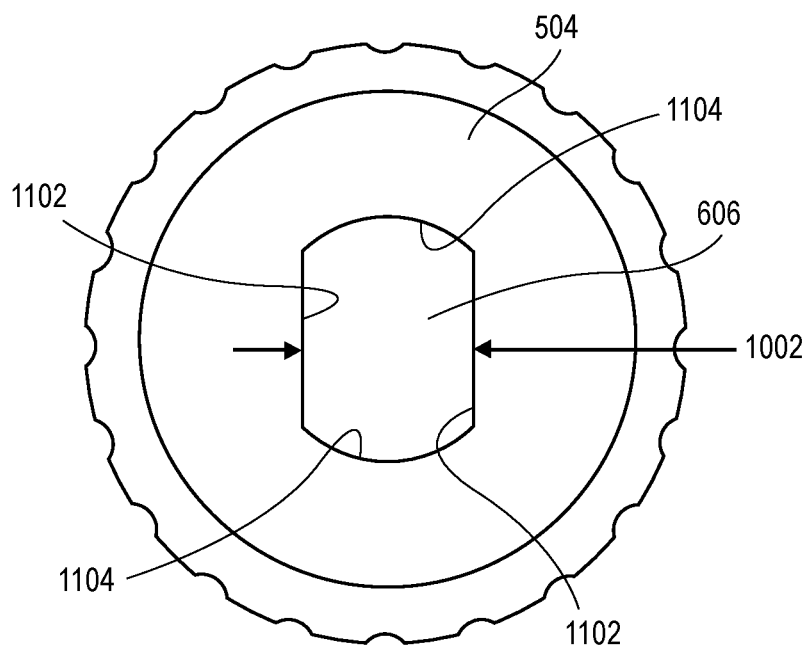
FIG. 11 is an end view of a tool cap, in accordance with an embodiment.

Referring to FIG. 11, an end view of a tool cap is shown in accordance with an embodiment. Alternative structures for decreasing the ease of removing the valve bypass tool 312 from the protective sheath 308 are contemplated. By way of example, the cap lumen 606 that extends longitudinally through the tool cap 504 can have a non-circular profile and includes a first set of sides 1102 that are separated by the minimum cap lumen dimension 1002, and a second set of sides 1104 that are separated by a dimension that is greater than the minimum cap lumen dimension 1002. The profile can allow the tool cap 504 to contact the protective sheath 308 over less than the entire circumference of the protective sheath 308 while the protective sheath 308 is moving or sliding through the cap lumen 606. When the atraumatic end 310 of the protective sheath 308 engages the sides of the tool cap 504 surrounding the cap lumen 606, the interference between the tool cap 504 and the protective sheath 308 can resist removal of the protective sheath 308 from the valve bypass tool 312. In essence, the profile of the opening in the tool cap 504 can balance the force required to actuate the valve bypass tool 312 over the protective sheath 308 with the force required to remove the valve bypass tool 312 from the protective sheath 308. It is contemplated that the profile can minimize the former while maximizing the latter. Accordingly, the force required to actuate the valve bypass tool 312 over the protective sheath 308 may not be so high that it requires a user to push on the biostimulator transport system 300 with sufficient force to bend or kink the system. Yet the force required to remove the valve bypass tool 312 from the protective sheath 308 may be higher than a predetermined ergonomic threshold.

Figure 12:
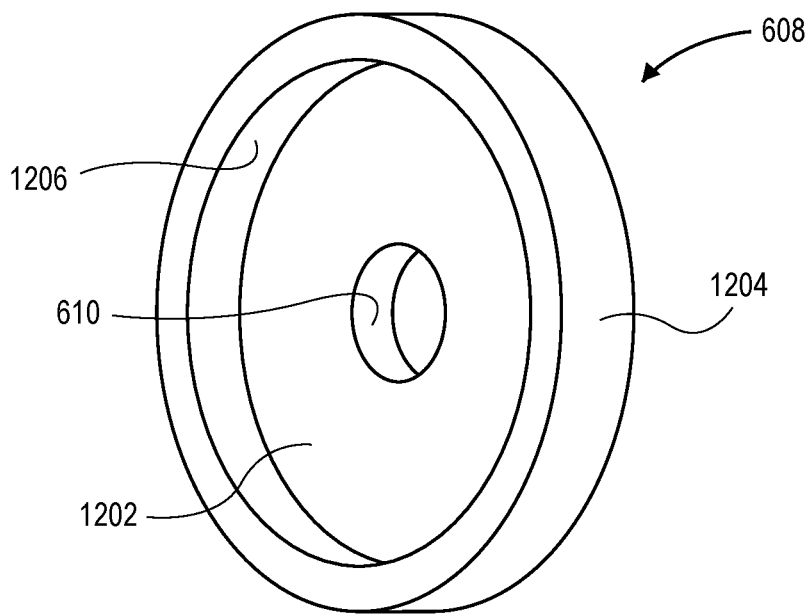
FIG. 12 is a perspective view of a tool seal, in accordance with an embodiment.

Referring to FIG. 12, a perspective view of a tool seal is shown in accordance with an embodiment. The annular seal 608 may include an annular disk 1202 having an outer profile at an outer wall 1204 of the seal, and an inner profile surrounding the seal lumen 610. In an embodiment, the annular seal 608 includes a seal flange 1206 extending longitudinally from the annular disk 1202. For example, seal flange 1206 can be a tubular section extending in the distal direction from the annular disk 1202. The seal flange 1206 can have an inner diameter that is greater than a diameter of the seal lumen 610. The seal flange 1206 can be mounted on a corresponding protrusion of the tool body 502. Accordingly, the seal flange 1206 can maintain a radial orientation of the annular seal 608 relative to the tool body 502, e.g., can prevent shifting of the annular seal 608 in the radial direction. As described above, the annular seal 608, e.g., the seal flange 1206, can be compressed between the tool cap 504 and the tool body 502 to retain the annular seal 608 within the valve bypass tool 312.

Figure 13:
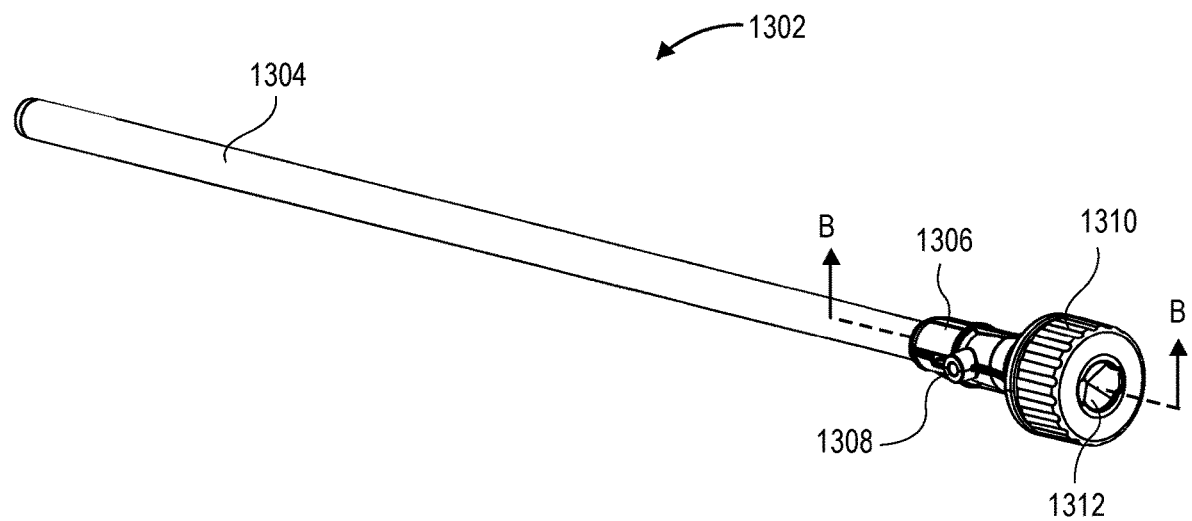
FIG. 13 is a perspective view of an access introducer, in accordance with an embodiment.

Referring to FIG. 13, a perspective view of an access introducer is shown in accordance with an embodiment. An access introducer 1302 having a lock feature can be used in combination with the valve bypass tool 312 or another component. For example, a dilator having a locking tabs 520 similar to the male coupling described above could be used in combination with the access introducer 1302 to provide an introducer set.

The access introducer 1302 can include an introducer catheter 1304 extending distally from an introducer body 1306. The introducer catheter 1304 can be an elongated tubular member having an internal lumen sized to receive and allow passage of the biostimulator transport system 300 and/or the biostimulator 100. For example, the introducer catheter 1304 can be a 25 Fr tubular member. The introducer body 1306 can have an introducer side port 1308, which may be attached to an introducer flush port (not shown). More particularly, the introducer flush port can have a fluid fitting, e.g., luer-type fitting, connected to a flush line that connects to the introducer side port 1308. This structure is similar to the introducer flush port of the valve bypass tool 312 described above.

The access introducer 1302 can includes an introducer cap 1310 having a locking coupling to mate with the locking coupling of the valve bypass tool 312. The introducer cap 1310 may be mounted on the introducer body 1306. In an embodiment, an introducer seal 1312 is disposed between the introducer cap 1310 and the introducer body 1306. The introducer cap 1310 can be coupled to the introducer body 1306 by a weld joint or a threaded connection to retain the introducer seal 1312 between the cap and the body.

Figure 14:
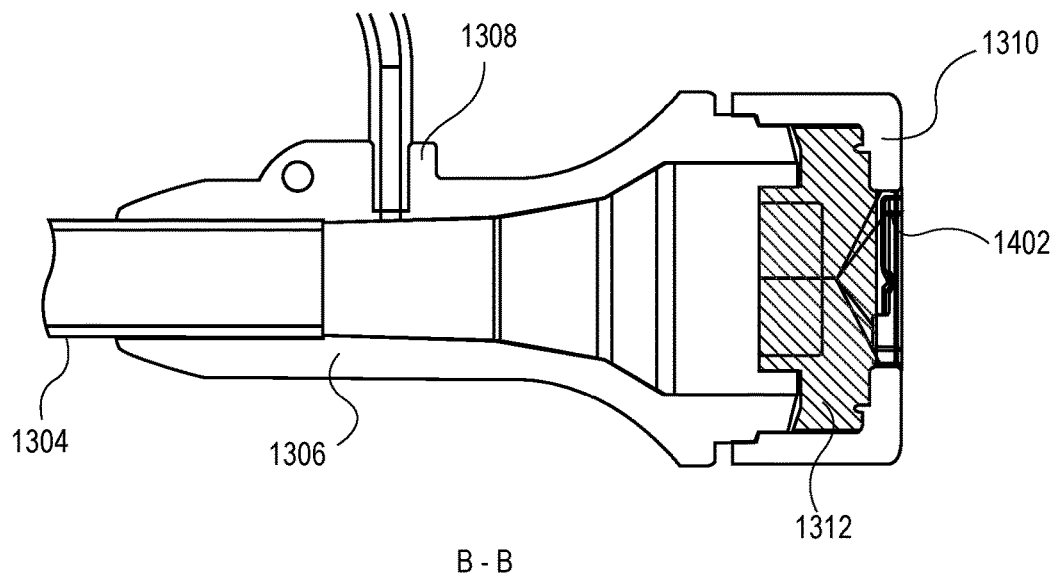
FIG. 14 is a cross-sectional view, taken about line B-B of FIG. 13, of an access introducer, in accordance with an embodiment.

Referring to FIG. 14, a cross-sectional view, taken about line B-B of FIG. 13, of an access introducer is shown in accordance with an embodiment. The introducer cap 1310 can have a proximal opening 1402 that provides access into the introducer body 1306 and the introducer catheter 1304. More particularly, the introducer seal 1312 can be exposed through the proximal opening 1402 such that the leadless pacemaker and/or biostimulator transport system 300 can be inserted into the access introducer 1302 through the opening and seal. In an embodiment, the introducer seal 1312 includes one or more slits, e.g., a cross-slit, that provides a passage from a proximal side of the seal to a distal side of the seal. The bypass sheath 506 can insert into the proximal opening 1402 and through the slit seal to establish a pathway that the leadless pacemaker 100 or the catheter components of the biostimulator transport system 300 can advance through.

Figure 15:
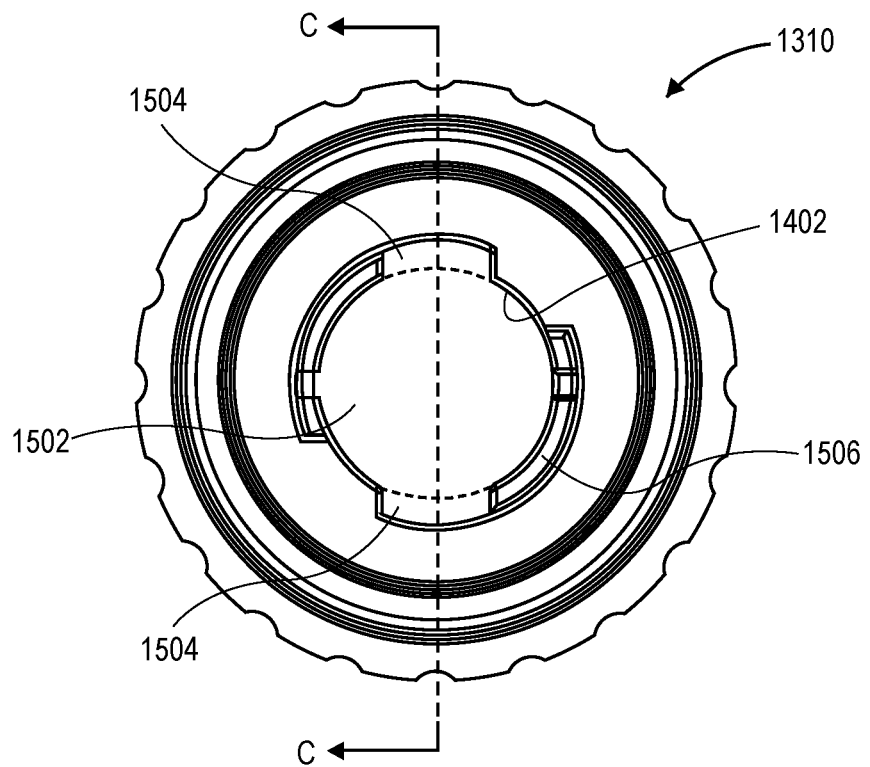
FIG. 15 is an end view of an introducer cap, in accordance with an embodiment.

Referring to FIG. 15, an end view of an introducer cap, in accordance with an embodiment. The proximal opening 1402 of the introducer cap 1310 can have a profile that permits insertion of the locking tabs 520 of the valve bypass tool 312 in a first orientation, and the rotation of the valve bypass tool 312 to cause an interference between the locking tabs 520 and the introducer cap 1310. The profile can have a central hole 1502 that is sized to receive the distal lip 806 of the tool body 502. For example, the central hole can have a diameter that is larger than a diameter of the distal lip 806. The profile can include one or more tab slots 1504 that have a profile that is similar and slightly larger than the locking tabs 520. The tab slots can be a region of the central opening radially outward from a circular profile of the central hole (radially outward from the dotted lines encircling the central hole). The locking tabs 520 can be inserted through the tab slots to insert the distal lip 806 through the introducer cap 1310.

The locking coupling of the access introducer 1302 can be a female coupling. For example, the introducer cap 1310 can include a locking groove 1506 sized and configured to receive the locking tabs 520. More particularly, when the valve bypass tool 312 is twisted after inserting the locking tabs 520 through the tab slots, the locking tabs 520 can be positioned distally and axially aligned with a portion of the introducer cap 1310 proximal to the locking tabs 520. The portion of the introducer cap 1310 can interfere with the locking tabs 520 when the locking tabs 520 is in the locking groove 1506. Accordingly, the locking tabs 520 engages the locking groove 1506 in the introducer cap 1310 to lock the valve bypass tool 312 to the access introducer 1302.

Figure 16:
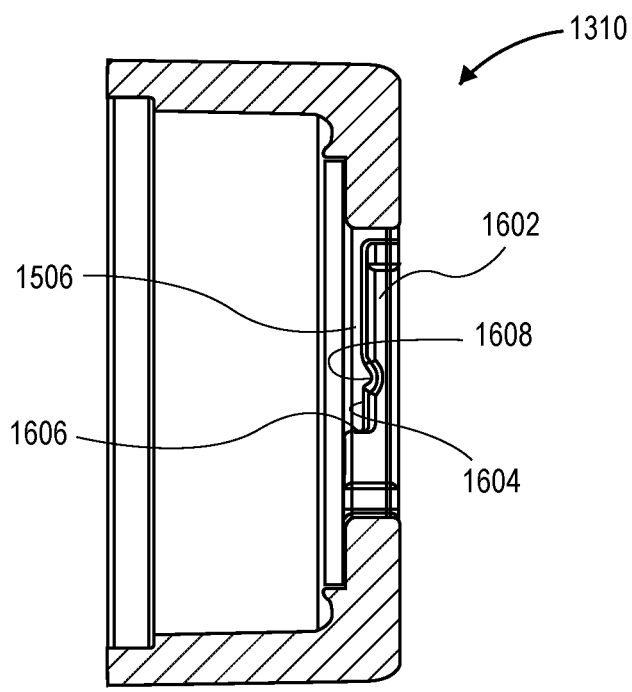
FIG. 16 is a cross-sectional view, taken about line C-C of FIG. 15, of an introducer cap, in accordance with an embodiment.

Referring to FIG. 16, a cross-sectional view, taken about line C-C of FIG. 15, of an introducer cap is shown in accordance with an embodiment. The portion of the introducer cap 1310 that resists proximal movement of the locking tabs 520 may be termed a ledge 1602. The locking groove 1506 can be a space distal to the ledge 1602 within which the locking tabs 520 move when the valve bypass tool 312 is rotated relative to the access introducer 1302. For example, the ledge 1602 can have a groove face 1604 that apposes the tab face 810 of the locking tabs 520 when the locking tabs 520 engages the locking groove 1506.

As the locking tabs 520 move through the locking groove 1506, e.g., when the locking tabs 520 engage the locking groove 1506 to lock the valve bypass tool 312 to the access introducer 1302, the tab face 810 of the locking tabs 520 may be in contact with the groove face 1604 of the locking groove 1506. For example, the detent 812 can slide over the groove face 1604 and bias the locking tabs 520 in the distal direction, e.g., away from the ledge 1602. When the valve bypass tool 312 is rotated fully, e.g., 90 degrees, after insertion into the introducer cap 1310, the lateral face of the locking tabs 520 can engage an end face 1606 of the locking groove 1506. Accordingly, the end face 1606 can stop further rotation of the valve bypass tool 312 by blocking movement of the locking tabs 520.

In an embodiment, the locking groove 1506 includes a recess 1608. The recess 1608 can be in the groove face 1604, e.g., extending proximally such that a proximalmost point of the recess 1608 is proximal to the groove face 1604. The recess 1608 provides a dimple within which the nub of the locking tabs 520 can rest. More particularly, when the valve bypass tool 312 is locked into the access introducer 1302, the detent 812 can extend into the recess 1608, which has a surface that conforms to a surface of the detent 812. The conforming surfaces mate in the locked position to resist disengagement of the valve bypass tool 312 from the access introducer 1302.

Referring to FIG. 17, a flowchart of a method of locking a valve bypass tool to an access introducer is shown in accordance with an embodiment. Having discussed the access introducer 1302 and the valve bypass tool 312 of the biostimulator transport system 300 above, a method of locking the biostimulator transport system 300 to the access introducer 1302 can now be described. The access introducer 1302 can be inserted into a patient through an incision site. The valve bypass tool 312 can be advanced over the protective sheath 308 to a fully distal position. In the fully distal position, the valve bypass tool 312 can cover the atraumatic end 310 of the protective sheath 308 and/or the leadless pacemaker 100.

At operation 1702, the bypass sheath 506 of the valve bypass tool 312 is inserted into the proximal opening 1402 of the access introducer 1302. In an embodiment, inserting the bypass sheath 506 into the proximal opening 1402 includes pushing on the push tab(s) 522 to force the bypass sheath 506 through the introducer seal 1312. As described above, the bypass sheath 506 includes a thin wall that advantageously allows the bypass sheath 506 to be inserted into the access introducer 1302 while both the leadless pacemaker 100 and the protective sheath 308 are positioned within the central lumen of the valve bypass tool 312. In other words, the leadless pacemaker and the protective sheath 308 do not have to be staggered to pass through the valve bypass tool 312 into the access introducer 1302 and the patient.

At operation 1704, the valve bypass tool 312 is twisted relative to the access introducer 1302 such that locking tabs 520, which passed through the tab slots 1504 of the introducer cap 1310, are rotated within the locking groove 1506. The user can press on the push tab(s) 522 to apply the torque that rotates the valve bypass tool 312. During rotation, the locking tabs 520 can engage the locking groove 1506 in the introducer cap 1310 to secure the valve bypass tool 312 to the access introducer 1302.

When the valve bypass tool 312 is locked to the access introducer 1302, the biostimulator transport system 300 and/or biostimulator 100 can be advanced into the patient. Advancement of the components can be achieved with a reduced likelihood that the valve bypass tool 312 will back out of the access introducer 1302 because the locking tabs 520 are held in place by the ledge 1602 of the introducer cap 1310. An interventional procedure can be completed, e.g., the biostimulator 100 can be delivered or retrieved by the biostimulator transport system 300, and the biostimulator transport system 300 can then be retrieved from the patient. For example, biostimulator transport system 300 can be retracted until the atraumatic end 310 of the protective sheath 308 is contained within the central lumen of the valve bypass tool 312, and the valve bypass tool 312 can be rotated to an unlocked position, e.g., in a counterclockwise direction, to release the valve bypass tool 312 from the access introducer 1302. The biostimulator transport system 300 and/or the access introducer 1302 can be removed from the patient to end the interventional procedure.

In the foregoing specification, the invention has been described with reference to specific exemplary embodiments thereof. It will be evident that various modifications may be made thereto without departing from the broader spirit and scope of the invention as set forth in the following claims. The specification and drawings are, accordingly, to be regarded in an illustrative sense rather than a restrictive sense.

What is claimed is:

1. A biostimulator transport system, comprising:
a handle;
a deflectable catheter extending from the handle to a distal catheter end;
a protective sheath slidably mounted on the deflectable catheter, wherein the protective sheath includes an atraumatic distal end having an outer dimension; and
a valve bypass tool slidably mounted on the protective sheath proximal to the atraumatic distal end, wherein the valve bypass tool includes an annular seal in sliding contact with the protective sheath, a locking tab extending radially outward from a tool body, and wherein the valve bypass tool includes a minimum lumen dimension that is less than the outer dimension of the atraumatic distal end of the protective sheath.

2. The biostimulator transport system of claim 1, wherein the locking tab includes a detent extending from a tab face.

3. The biostimulator transport system of claim 1, wherein the valve bypass tool includes a tool cap mounted on the tool body, and wherein the annular seal is between the tool cap and the tool body such that a seal lumen of the annular seal is aligned with a cap lumen of the tool cap and a body lumen of the tool body.

4. The biostimulator transport system of claim 3, wherein the cap lumen includes a minimum cap lumen dimension, and wherein the minimum cap lumen dimension is the minimum lumen dimension of the valve bypass tool.

5. The biostimulator transport system of claim 1, wherein the valve bypass tool includes a bypass sheath having a tubular wall around a bypass lumen, and wherein the tool body is mounted on the tubular wall.

6. The biostimulator transport system of claim 5, wherein the bypass sheath is metallic, wherein the tool body is polymeric, and wherein the tool body is overmolded onto the tubular wall.

7. The biostimulator transport system of claim 1, wherein the valve bypass tool includes a push tab extending radially outward from the tool body to an outer tab face, and wherein a radial dimension between the tool body and the outer tab face is greater than a longitudinal dimension of the outer tab face.

8. The biostimulator transport system of claim 1, wherein the biostimulator transport system is a biostimulator delivery system including a tether extending through the deflectable catheter.

9. The biostimulator transport system of claim 1, wherein the biostimulator transport system is a biostimulator retrieval system including a snare extending through the deflectable catheter.

10. A valve bypass tool, comprising:
a tool body having a body lumen;
a tool cap mounted on the tool body and having a cap lumen;
an annular seal having a seal lumen aligned with the body lumen and the cap lumen;
a locking tab extending radially outward from the tool body; and
a bypass sheath having a tubular wall around a bypass lumen, wherein the bypass lumen is aligned with the body lumen, the seal lumen, and the cap lumen, and wherein the tool body is mounted on the tubular wall.

11. The valve bypass tool of claim 10, wherein the locking tab includes a detent extending from a tab face.

12. The valve bypass tool of claim 10, wherein the tool cap is welded to the tool body.

13. The valve bypass tool of claim 10, wherein the cap lumen includes a minimum cap lumen dimension that is larger than a seal lumen dimension of the seal lumen.

14. The valve bypass tool of claim 10, wherein the bypass sheath is metallic, wherein the tool body is polymeric, and wherein the tool body is overmolded onto the tubular wall.

15. The valve bypass tool of claim 14 further comprising a push tab extending radially outward from the tool body to an outer tab face, wherein a radial dimension between the tool body and the outer tab face is greater than a longitudinal dimension of the outer tab face.

16. A method, comprising:
inserting a bypass sheath of a valve bypass tool into a proximal opening of an introducer cap of an access introducer, wherein the valve bypass tool is slidably mounted on a protective sheath of a biostimulator transport system, and wherein the valve bypass tool includes an annular seal in sliding contact with the protective sheath; and
twisting the valve bypass tool relative to the access introducer such that a locking tab of the valve bypass tool engages the introducer cap.

17. The method of claim 16, wherein inserting the bypass sheath into the proximal opening includes pushing on a push tab of the valve bypass tool.

18. The method of claim 16, wherein the locking tab has a tab face in contact with a groove face of the introducer cap when the locking tab engages the introducer cap to lock the valve bypass tool to the access introducer.

19. The method of claim 18, wherein the locking tab includes a detent extending from the tab face into a recess in the groove face.

* * * * *